United States Patent
Eimer et al.

(10) Patent No.: US 11,986,342 B2
(45) Date of Patent: May 21, 2024

(54) CHARACTERIZATION OF CARDIAC SHUNTS WITH BUBBLES

(71) Applicant: Agitated Solutions Inc., Oakdale, MN (US)

(72) Inventors: Micah J Eimer, Glenview, IL (US); Morgan Evans, Apple Valley, MN (US); Benjamin Arcand, Minneapolis, MN (US); Jennifer Chmura, Minneapolis, MN (US); C. Lance Boling, San Jose, CA (US)

(73) Assignee: Agitated Solutions Inc., St. Paul, MN (US)

(*) Notice: Subject to any disclaimer, the term of this patent is extended or adjusted under 35 U.S.C. 154(b) by 104 days.

(21) Appl. No.: 17/321,957

(22) Filed: May 17, 2021

(65) Prior Publication Data

US 2021/0361257 A1    Nov. 25, 2021

Related U.S. Application Data

(60) Provisional application No. 63/026,177, filed on May 18, 2020.

(51) Int. Cl.
*A61B 8/08* (2006.01)
*A61B 8/06* (2006.01)

(52) U.S. Cl.
CPC ............ *A61B 8/0883* (2013.01); *A61B 8/065* (2013.01); *A61B 8/481* (2013.01)

(58) Field of Classification Search
CPC ............................. G01S 7/52039; A61B 8/481
See application file for complete search history.

(56) References Cited

U.S. PATENT DOCUMENTS

| 2006/0264759 A1* | 11/2006 | Moehring | ................ A61B 8/06 600/469 |
| 2011/0082373 A1* | 4/2011 | Gurley | .................... A61B 8/06 600/454 |

OTHER PUBLICATIONS

Soliman et al. (2007). The use of contrast echocardiography for detection of cardiac shunts. Eur J Echocardiogrpahy, 8, S2-S12. doi:10.1016/j.euje.2007.03.006. (Year: 2007).*

(Continued)

*Primary Examiner* — Angela M Hoffa
*Assistant Examiner* — Younhee Choi
(74) *Attorney, Agent, or Firm* — Matthew J. Smyth

(57) ABSTRACT

A method may include intravenously directing first bubbles into a patient's venous circulatory system and to a right side of the patient's heart. The first bubbles may have sizes that fall within a first range. The method may further include monitoring the patient's heart, with ultrasound imaging, to detect presence of the first bubbles on a left side of the patient's heart. Upon detecting the first bubbles on the left side of the patient's heart, the method may further include intravenously directing second bubbles into the patient's venous circulatory system and to the right side of the patient's heart. The second bubbles may have sizes that fall within a second range that is different than the first range. Upon detecting the second bubbles on the left side of the patient's heart, the method may further include initiating treatment to minimize risk of stroke in the patient.

7 Claims, 4 Drawing Sheets

(56) References Cited

OTHER PUBLICATIONS

Zhao et al. (2017). Comparison of Different Contrast Agents in Detecting Cardiac Right-to-Left Shunt in Patients with a Patent Foramen Ovale during Contrast-Transthoracic Echocardiography. BioMed Research International, vol. 2017, Article ID 6086094. doi.org/10.1155/2017/6086094. (Year: 2017).*

Bernard et al., "Agitated Saline Contrast Echocardiography in the Identification of Intra- and Extracardiac Shunts: Connecting the Dots," Journal of the American Society of Echocardiography, 2020, 1-11, doi: 10.1016/j.echo.2020.09.013.

Hackett, Heather, et al. "A methodological approach for quantifying and characterizing the stability of agitated saline contrast: Implications for quantifying intrapulmonary shunt". Journal of Applied Physiology, vol. 121, No. 2, 2016, p. 568-576. https://doi.org/10.1152/japplphysiol.00422.2016.

Jiang, Weijian, et al. "Establishment of a porcine model of patent foramen ovale". Neurological Research, vol. 28, No. 1, 2006, p. 82-86. https://doi.org/10.1179/016164106x91924.

Masoero, Giovanni, et al. "Agitated saline contrast echocardiography reveals a systemic-to-pulmonary venous shunt". Echocardiography, vol. 35, No. 5, 2018, p. 747-749. https://doi.org/10.1111/echo.13859.

Pinto, Fausto. "When and how to diagnose patent foramen ovale". Heart, vol. 91, No. 4, 2005, p. 438-440. https://doi.org/10.1136/hrt.2004.052233.

Stickland, Michael, et al. "Intra-Pulmonary Arteriovenous Anastomoses and Pulmonary Gas Exchange: Evaluation by Microspheres, Contrast Echocardiography and Inert Gas Elimination". The Journal of Physiology, vol. 597, No. 22, 2019, p. 5365-5384. https://doi.org/10.1113/jp277695.

Attaran, Robert, et al. "Protocol for optimal detection and exclusion of a patent foramen ovale using transthoracic echocardiography with agitated saline microbubbles". Echocardiography, vol. 23, No. 7, 2006, p. 616-622. https://doi.org/10.1111/j.1540-8175.2006.00272.x.

Arndt, J., et al. "Agitated saline contrast echocardiography to diagnose a congenital heart defect in a dog". Journal of Veterinary Cardiology, vol. 10, No. 2, 2008, p. 129-132. https://doi.org/10.1016/j.jvc.2008.03.004.

Collado et al., Patent Foremen Ovale Closure for Stroke Prevention and Other Disorders, 2018, Journal of the American Heart Association, 7:e007146, doi:10.1161/JAHA.117.007146.

Muskula and Main, "Safety With Echocardiographic Contrast Agents," Circulation: Cardiovascular Imaging, 2017, 10:e005459, doi:10.1161/CIRCIMAGING.116.005459.

Pasupathy et al., "Nanobubbles: A Novel Targeted Drug Delivery System," Brazilian Journal of Pharmaceutical Sciences, 2022, 58:e19608, doi:10.1590/s2175-97902022e19604.

Kabha and Barak. "Paradoxical symptomatic air embolism after saline contrast transesophageal echocardiography". Echocardiography, vol. 25, No. 3, 2008, p. 349-350. https://doi.org/10.1111/j.1540-8175.2007.00628.x.

Tsivgoulis et al., "Safety of TCD 'Bubble Study'", Stroke, 2010, 41:e195, doi:10.1161/STROKEAHA.109.562793.

Cabrelli et al., "Stable phantom materials for ultrasound and optical imaging," Physics in Medicine and Biology, 2017, 432-447, doi:10.1088/1361-6560/62/2/432.

Lindner, A Practical Approach to Contrast Echocardiography, 2017, American College of Cardiology, https://www.acc.org/latest-in-cardiology/articles/2017/07/10/09/17/a-practical-approach-to-contrast-echocardiography, accessed Apr. 20, 2022.

Stride, E, and N Saffari. "Microbubble ultrasound contrast agents: a review." Proceedings of the Institution of Mechanical Engineers. Part H, Journal of engineering in medicine vol. 217,6 (2003): 429-47. doi:10.1243/09544110360729072.

Bassett, GC, et al. "Evaluating the potential risks of bubble studies during echocardiography". Perfusion, vol. 30, No. 3, 2014, p. 219-223. https://doi.org/10.1177/0267659114539182.

Kumar et al., "Micro-Bubbles in the Left Heart," Journal of Cardiology & Cardiovascular Therapy, 2017, vol. 8, Issue 5, 1-4, doi: 10.19080/JOCCT.2017.08.555748.

Lin et al., "Optimizing Sensitivity of Ultrasound Contrast-Enhanced Super-Resolution Imaging by Tailoring Size Distribution of Microbubble Contrast Agent," Ultrasound in Medicine and Biology, 2017, vol. 43, No. 10, 2488-2493, doi:10.1016/j.ultrasmedbio.2017.05.014.

Hara, Hidehiko, et al. "Patent foramen ovale: standards for a preclinical model of prevalence, structure, and histopathologic comparability to human hearts". Catheterization and Cardiovascular Interventions, vol. 69, No. 2, 2006, p. 266-273. https://doi.org/10.1002/ccd.20973.

Jalal, Zakaria, et al. "Role of animal models for percutaneous atrial septal defect closure". Journal of Thoracic Disease, vol. 10, No. S24, 2018, p. S2966-S2974. https://doi.org/10.21037/jtd.2018.07.119.

* cited by examiner

CHARACTERIZATION OF CARDIAC SHUNTS WITH BUBBLES

CROSS-REFERENCE TO RELATED APPLICATIONS

This application claims the benefit of U.S. Provisional Application Ser. No. 63/026,177, titled "Characterization of Cardiac Shunts with Bubbles," filed May 18, 2020. This application incorporates the entire contents of the foregoing application herein by reference.

TECHNICAL FIELD

Various embodiments relate generally to diagnosing and characterizing cardiac shunts.

BACKGROUND

A patent foramen ovale (PFO) or atrial septal defect (ASD) may be present in the septum that would otherwise separate two sides of a patient's heart. When present, either a PFO or an ASD can allow embolic material—which would otherwise be filtered out by the patient's lungs but for the PFO or ASD—to enter arterial circulation.

SUMMARY

In some implementations, a method includes intravenously directing first bubbles into a patient's venous circulatory system and to a right side of the patient's heart. The first bubbles may have sizes that fall within a first range. The method may further include monitoring the patient's heart, with ultrasound imaging, to detect presence of the first bubbles on a left side of the patient's heart. Upon detecting the first bubbles on the left side of the patient's heart, the method may further include intravenously directing second bubbles into the patient's venous circulatory system and to the right side of the patient's heart. The second bubbles may have sizes that fall within a second range, and the second range may have sizes that are greater than sizes in the first range. The method may further include monitoring the patient's heart, with ultrasound imaging, to detect presence of the second bubbles on a left side of the patient's heart. Upon detecting the second bubbles on the left side of the patient's heart, the method may further include intravenously directing third bubbles into the patient's venous circulatory system and to the right side of the patient's heart. The third bubbles may have sizes that fall within a third range, and the third range may have sizes that are greater than sizes in the second range. Upon detecting the third bubbles on the left side of the patient's heart, the method may further include initiating treatment to minimize risk of stroke in the patient.

Intravenously directing first bubbles may include injecting an agitated solution of saline or dextrose into a median cubital vein of the patient. Monitoring the patient's heart with ultrasound imaging may include conducting either a transthoracic echocardiogram (TTE) or a transesophageal echocardiogram (TEE). Initiating treatment may include administering a blood thinner to the patient. Initiating treatment may include surgically closing a shunt in the patient's heart using a catheter-delivered percutaneous closure device.

In some implementations, the first range comprises bubbles having diameters approximately between 8 um and 15 um. In some implementations, the second range comprises bubbles having diameters approximately between 15 um and 25 um. In some implementations, the third range comprises bubbles having diameters approximately between 25 um and 35 um.

In some implementations, a method may include intravenously directing first bubbles into a patient's venous circulatory system and to a right side of the patient's heart. The first bubbles may have sizes that fall within a first range. The method may further include monitoring the patient's heart, with ultrasound imaging, to detect presence of the first bubbles on a left side of the patient's heart. Upon detecting the first bubbles on the left side of the patient's heart, the method may further include intravenously directing second bubbles into the patient's venous circulatory system and to the right side of the patient's heart. The second bubbles may have sizes that fall within a second range. The second range may have sizes that are different than sizes in the first range. Upon detecting the second bubbles on the left side of the patient's heart, the method may further include initiating treatment to minimize risk of stroke in the patient.

Initiating treatment may include administering a blood thinner to the patient. Initiating treatment may include surgically closing a shunt in the patient's heart using a catheter-delivered percutaneous closure device. In some implementations, the method further includes determining a blood flow rate, using ultrasound imaging. Determining a blood flow rate may include monitoring movement of first bubbles or second bubbles within the patient's heart.

DETAILED DESCRIPTION

Agitated saline contrast studies are a useful adjunct to many ultrasound examinations, particularly cardiac ultrasound (echocardiography). Injection of agitated saline into a vein combined with echocardiography may be used to detect shunts which may be within the heart, such as a patent foramen ovale (PFO) or an atrial septal defect (ASD) (two types of holes in the heart), or external to the heart (e.g., in the lungs) known as pulmonary arteriovenous malformations (pAVM). Agitated saline can also be used with echocardiography to confirm catheter placement in fluid around the heart (pericardiocentesis), detect anomalous connections within the heart, visualize the right side of the heart, and accentuate right-sided blood flow for the purpose of quantitation.

Agitated saline contrast echocardiography takes advantage of the increased reflection that results when ultrasound waves meet a liquid/gas interface. This allows for visualization of otherwise poorly reflective areas such as fluid filled cavities by ultrasound imaging equipment. Applications in which this has been clinically useful include echocardiography where agitated saline can be used to define the structural integrity of the interatrial septum or infer the presence of a transpulmonary shunt. Agitated saline can also be combined with Doppler echocardiography to assess blood flow through the tricuspid valve. An alternative method to detect atrial defects uses ultrasound of the brain vessels (transcranial Doppler) to detect bubbles that have crossed from the right heart to the left heart and entered the cerebral circulation.

Figure 1:
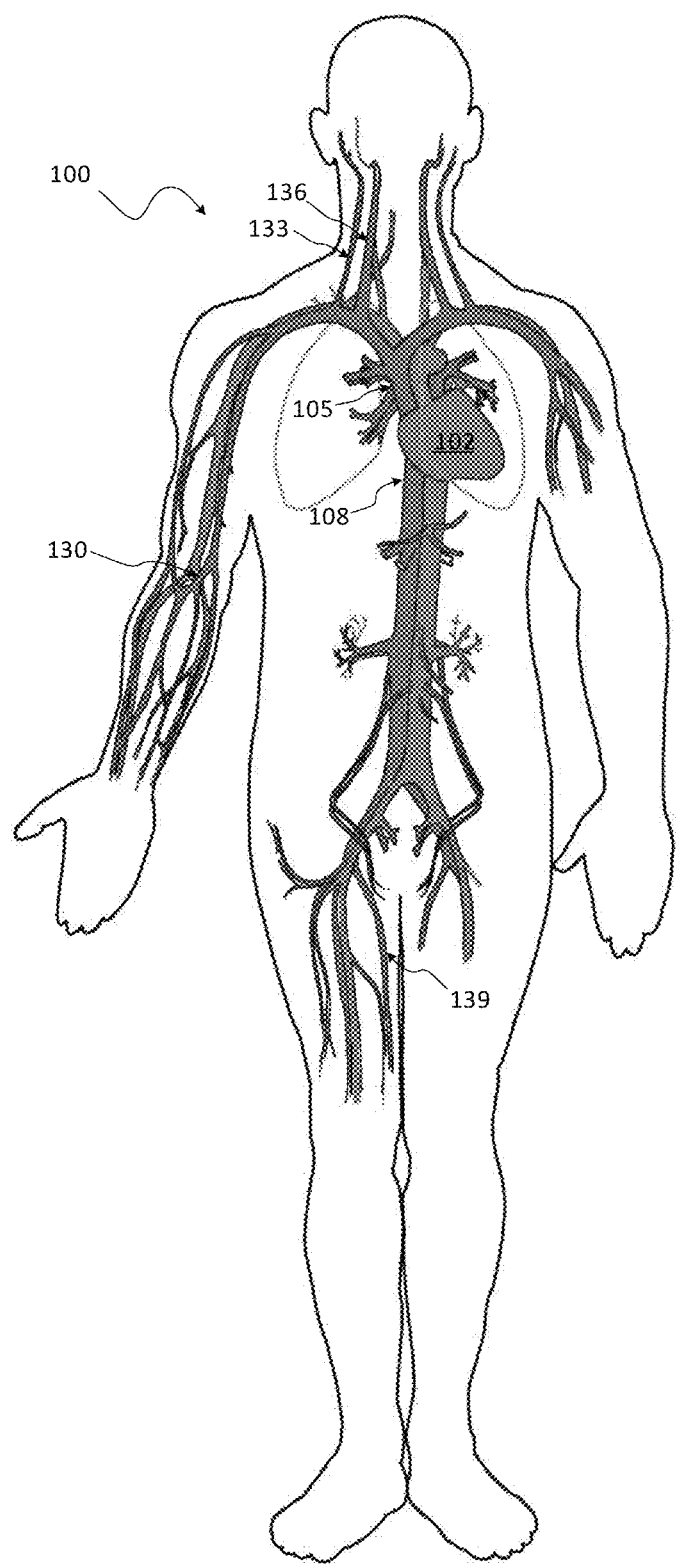
FIG. 1 illustrates a portion of a human circulatory system.

Described herein are methods for characterizing the extent of shunts, such as interatrial shunts. For context, various aspects of a human cardiovascular system are first described with reference to FIG. 1 and FIGS. 2A, 2B and 2C. FIG. 1 illustrates a portion of an overall human circulatory system 100. At its core, is the heart 102, and a system of arteries that extend from the heart, and veins that return to the heart.

Figure 2A:
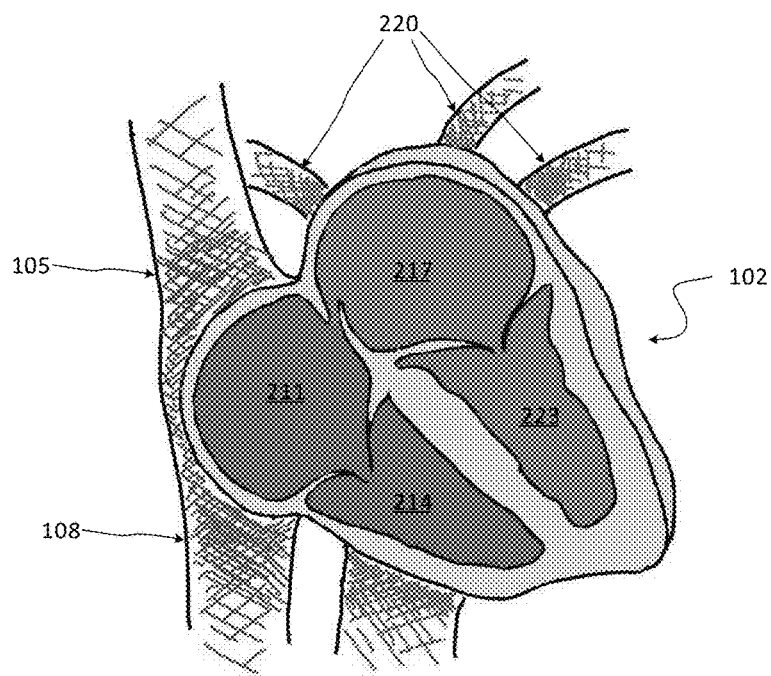
FIG. 2A illustrates detail of a human heart.

Various internal structures of the heart 102 are described in greater detail with reference to FIG. 2A. Blood is returned to the heart 102 from throughout the body by the vena cava, which is divided into the superior vena cava 105, which collects blood from the upper portion of the body, and the inferior vena cava 108, which collects blood from the lower portion of the body. Blood flows through the superior vena cava 105 and inferior cava 108 on its way to the right atrium 211.

After being oxygenated in the lungs, blood is returned to the left atrium 217 of the heart 102 via the pulmonary veins 220 (three of four of which are shown). From the left atrium 217, the heart 102 pumps blood into the left ventricle 223, which in turns pumps it to the aorta for distribution throughout the body.

Figure 2B:
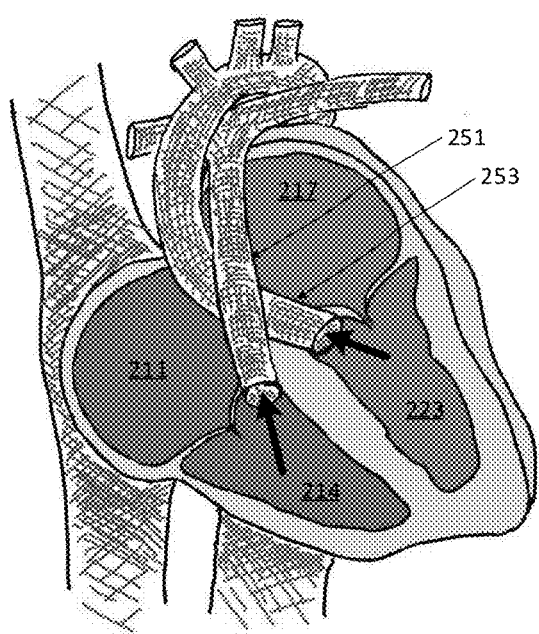
FIG. 2B depicts a ventricular systole phase of a heart.
Figure 2C:
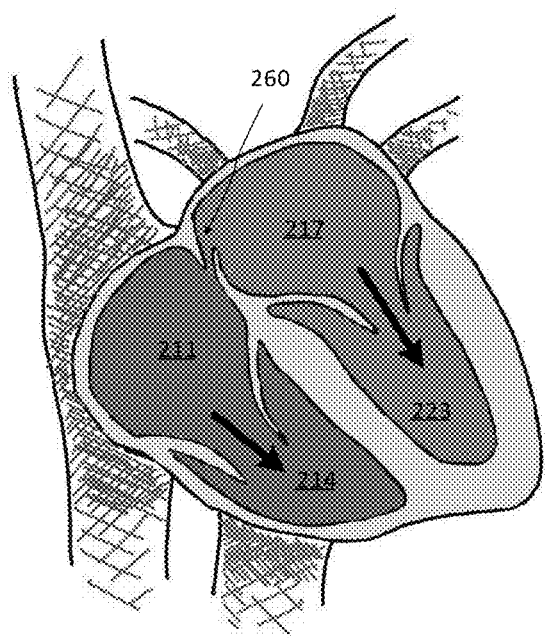
FIG. 2C depicts an atrial systole phase of a heart.

In more detail, with reference to FIG. 2B, the right ventricle 214 and left ventricle 223 contract during a ventricular systole phase, pumping blood from the right ventricle 214 into the pulmonary artery 251 and from the left ventricle 223 to the aorta 253. With reference to FIG. 2C, the left atrium 211 and right atrium 217 contract during an atrial systole phase, pumping blood from the right atrium 211 to the right ventricle 214 and from the left atrium 217 to the left ventricle 223. In FIG. 2C, the pulmonary artery 251 and aorta 253 have been removed to better illustrate intracardiac flow.

Also illustrated in FIG. 2C is a shunt 260 that fluidly couples the right atrium 211 and the left atrium 217. When present, such a shunt can increase a risk of stroke by allowing embolic material (e.g., a blood clot, a fat globule, other foreign material) to move from the right atrium 211 to the left atrium 217, then into the left ventricle 223, and finally into arterial circulation through the body via the aorta 253—where the embolic material can cause a stroke or other critical blockage. But for the presence of such a shunt 260, the embolic material would, in most patients, be filtered by the lungs.

Shunts may take different forms. For example, a PFO is a small flap-like opening that is normally present at birth in the heart wall (septum) that separates the left atrium from the right atrium. In some patients, this PFO never fully closes after birth. An ASD is a type of birth defect in which a hole exists in the septum dividing the atria. Often, an ASD is more serious than a PFO. Not illustrated, but also possible, is a ventricular septal defect (VSD), in which a hole exists in the septum that separates the right ventricle from the left ventricle.

When a shunt 260 is present in a patient's heart, the size of the shunt 260 may determine the risk of a traumatic or catastrophic effect of embolic material entering arterial circulation via the left atrium 217, left ventricle 223 and aorta 253, rather than being filtered out in the lungs. A larger shunt may, depending on other aspects of the patient's anatomy and physiology, allow larger emboli to enter arterial circulation, where such emboli could cause a stroke, heart attack or other traumatic blockage.

Many shunts can be treated—either surgically (e.g., with percutaneous closure using a catheter, or with open-heart surgery and direct surgical closure), or with medication (e.g., blood thinners, to reduce the risk of clots). However, many shunts need not be treated. That is, many shunts are small enough, and patients may be otherwise healthy enough that the reduction of risk by closing a small shunt may be outweighed by the risk of a procedure to close the shunt.

For example, in some patients with ASDs, where the ASD is less than 5 mm and there is no evidence of either right ventricular volume overload or paradoxical embolism, it may be safer to not surgically treat the ASD; on the other hand, ASDs that are larger than 5 mm or in patients where right ventricle overload is detected, or where the patient has suffered a cryptogenic stroke, surgical repair of the ASD may be indicated. Similarly, in some patients, surgical repair may be indicated for PFOs that exceed 4 mm in diameter, or in patients that have recently suffered a cryptogenic stroke. For these reasons, it can be advantageous to accurately assess the size of the shunt, in order to facilitate weighing of risks between repairing an ASD or PFO, or leaving it untreated surgically.

Whereas a single bubble study may be used to assess the presence of a cardiac shunt, additional diagnostic information can be obtained from multiple bubble studies, especially when it is possible to control for bubble size and progressively and predictably increase the size of bubbles from one bubble study to the next. A method for assessing size of a cardiac shunt is now described with reference to FIG. 3A, FIG. 3B and FIG. 3C.

Figure 3A:
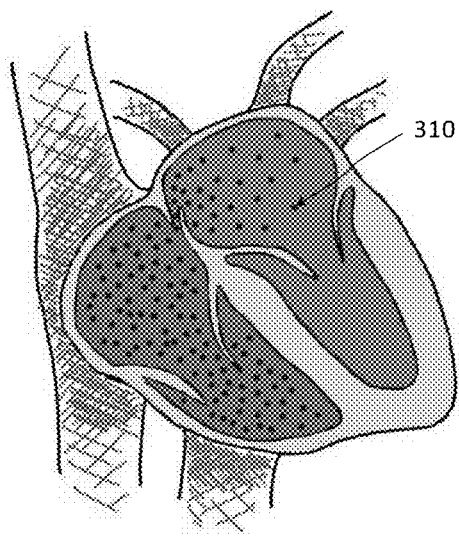
FIGS. 3A-3C depict bubble studies conducted with bubbles of varying sizes.
Figure 3B:
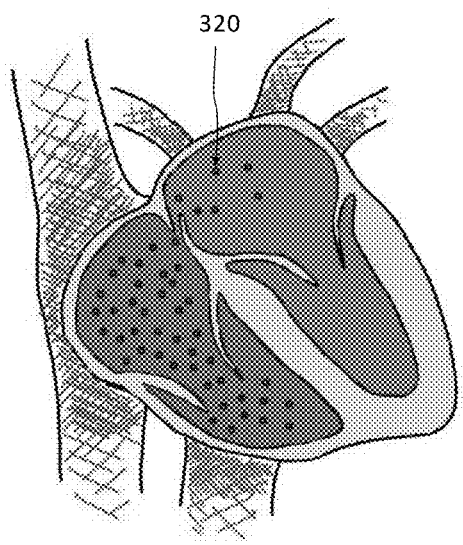
Figure 3C:
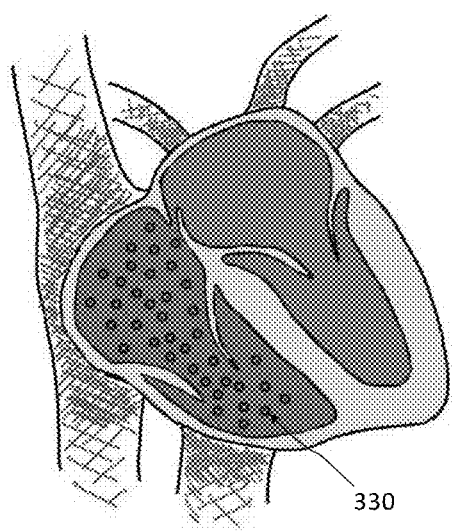

As depicted in FIG. 3A, a bubble study may be conducted using small bubbles 310 (e.g., bubbles having a diameter in the approximate range of 8 um to 15 um, where "approximate" may mean within 1%, 5%, 10%, 20%, 25% or 50% of a nominal value). Upon confirmation of a shunt (e.g., by detection of immediate (e.g., within one, two or three atrial systole phases) bubble migration from right atrium to left atrium, a second bubble study may be conducted using larger bubbles 320 (e.g., bubbles having a diameter in the approximate range of 15 um to 25 um), as depicted in FIG. 3B. In some cases, regardless of the outcome the second bubble study, a third bubble study, using still larger bubbles 330 (e.g., bubbles having a diameter in the approximate range of 25 um to 35 um), as depicted in FIG. 3C, may be conducted; in other cases, the third bubble study may only be conducted if a shunt is confirmed by the second bubble study.

Described above is a sequence of bubble studies in which the first study is with "small" bubbles and the last study is conducted with "large" bubbles. This order may also be reversed. For example, in some patients where a cardiac shunt is anticipated (e.g., following a cryptogenic stroke), a "large" bubble study may be conducted first. In such a case, if a suspected cardiac shunt is confirmed, no additional bubble studies may be required. Three bubble studies are described above, but in some cases, even when the first study involves small bubbles, only two bubble studies may be required. In some cases, multiple (e.g., two, three, four or more) bubble studies may be conducted using the same size bubbles. In some cases, different size bubbles may be used; for example, when the risk of inducing an air embolism is determined to be low for a specific patient, bubbles larger than 35 um may be employed. The methods described herein may be modified in order, repetition and in other ways, at the discretion of the medical care provider.

Figure 4:
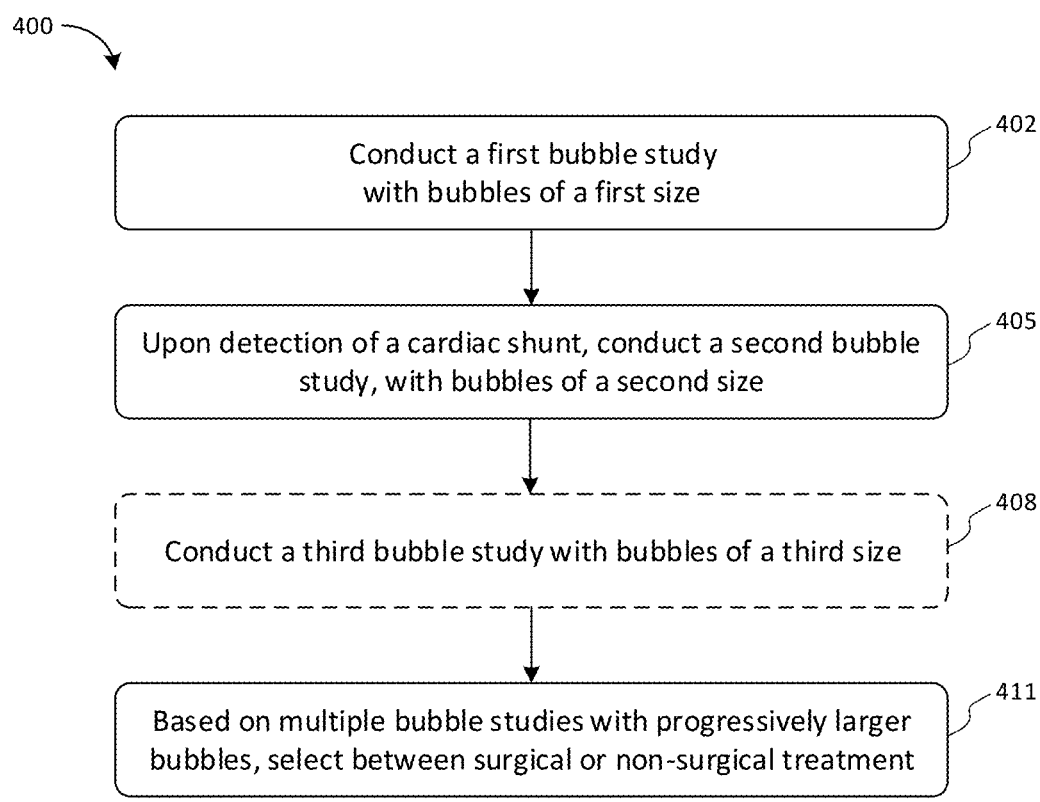
FIG. 4 illustrates a method for conducting multiple bubble studies in sequence to characterize a cardiac shunt.

FIG. 4 illustrates a method 400 for conducting a sequence of bubble studies. The method 400 includes conducting (402) a first bubble study with bubbles of a first size. For example, a bubble study with small bubbles 310, such as depicted in FIG. 3A, may be first conducted (402) to identify a shunt of any significant size. The first bubble study may be motivated by a stroke (e.g., a cryptogenic stroke, or stroke of unknown causes), or it may be part of a cardiac workup that is motivated by other reasons.

When a shunt is detected, for example by detection of bubbles on the left side of the heart (either in the left atrium or left ventricle) within one systole phase of their presence on the right side of the heart (or, in some implementations, within two or three atrial systole phases), the method 400 includes conducting (405) a second bubble study with bubbles of a second size. For example, a bubble study with larger bubbles 320, as depicted in FIG. 3B, may be conducted (405). Detection of these larger bubbles 320 on the left side of the heart can provide further information about the nature and extent of the shunt.

Optionally (and as a matter of course, in some cases, when bubbles in the second bubble study are detected on the left side of the heart), a third bubble study may be conducted (408) with still-larger bubbles. For example, the third bubble study may employ still-larger bubbles 330.

Based on the multiple studies with progressively larger bubbles, it may be possible to characterize a size or extent of a cardiac shunt; based on this characterization, the method 400 can include selecting (411) between surgical or non-surgical treatment of the shunt.

For example, if a first bubble study with small bubbles, such as the study depicted in FIG. 3A, identifies a shunt in a patient's heart, but bubbles are not detected on the left side of the patient's heart in a follow-on study with larger bubbles, and the patient has no other underlying health concerns that would make an unclosed shunt particularly high-risk, the shunt may be left untreated surgically. In some cases, the patient may be provided with a blood thinner, to reduce the risk of clots, or the patient may be provided with some other prophylactic medication. As another example, if bubble migration from right to left were detected in a patient in three bubble studies with progressively larger bubbles, it may be determined that a shunt of significant size is present, and surgical closure may be indicated.

By controlling the size of the bubbles (e.g., by generating them in a manner that results in relatively consistent and fixed sizing—for example, one in which a median bubble size may fall within a specified range, or in which a majority of bubbles within a distribution of bubble sizes may fall within one, two or three standard deviations of a specified range) and by measuring or inferring other cardiac parameters, such as blood volume and blood flow, it may be possible to characterize cardiac shunts in far greater detail than would otherwise be possible. In addition to detecting mere presence of bubbles of any given size, a volume or number of bubbles may also be measured. In this manner, particularly when bubble volume, blood volume and blood flow are all measured or inferred, it may be possible to characterize larger shunts, even if it is not possible (e.g., for safety reasons) to use very large bubbles alone to character such shunts.

Multiple techniques may be employed to detect the presence of bubbles on the left side of the heart. For example, a noninvasive transthoracic echocardiogram (TTE) may be employed, whereby an ultrasound transducer is placed on the chest of a patient undergoing the bubble study. High frequency soundwaves (ultrasound) are used to create a moving picture of the heart, through the chest wall, and when the ultrasound and bubble study are properly performed, bubbles that are present on either side of the heart will be picked up and imaged through the procedure.

A transesophageal echocardiogram (TEE) may also be employed for higher resolution of images. In a TEE, and ultrasound transducer is placed in the esophagus of the patient undergoing the procedure. Given the proximity of the esophagus to the heart, and given that the ultrasound in a TEE does not have to traverse the chest wall and rib cage, the images from a TEE are typically much clearer than with a TTE.

Machine learning algorithms may be employed across multiple bubble studies to provide additional diagnostic information. For example, precise measurements could be captured from the ultrasound images in ether TTE or TEE procedures, to determine blood volume in each chamber of a patient's heart. Individual bubbles could be traced to capture a blood flow rate. Regression analysis could be applied across many patients to determine likelihood of bubbles (or bubbles of a particular size) appearing on the left side of the patient's heart when a shunt is present, or a shunt of a particular kind, given specific volumes or flow rates. When such a shunt is identified and repaired, more precise information about its size could be gleaned during the procedure for its repair, and this information could be fed back into the machine learning algorithm. Other variables could be incorporated into such machine learning algorithms (e.g., patient age, other heart or general health conditions, respiratory function, gender, genetics, blood type, etc.).

To facilitate bubble studies or other diagnostic or therapeutic procedures whereby bubbles are to be introduced into the circulatory system, one must get the bubbles into the venous system and ultimately into the superior vena cava 105 or inferior vena cava 108, and into the right atrium 211 of the heart 102. With reference to FIG. 1, there are several common access points through which bubbles can be so introduced. Common among them is intravenous introduction of bubbles (e.g., mixed with saline or dextrose) via the median cubital vein 130 of the right arm. From here, blood flows through the basilic vein, axillary vein, subclavian vein, and into the superior vena cava 105. Alternative paths to the superior vena cava 105 are the external jugular vein 133, or internal jugular vein 136, both of which drain into the brachiocephalic vein prior to reaching the superior vena cava 105. An alternative inferior route includes the femoral vein 139, which flows into the inferior vena cava 108 prior to reaching the right atrium 211. Other routes to the right atrium 211 are possible.

While several implementations have been described with reference to exemplary aspects, it will be understood by those skilled in the art that various changes may be made and equivalents may be substituted for elements thereof without departing from the contemplated scope. For example, described herein are methods for characterizing cardiac shunts. The methods could easily be adapted, however, to identify shunts or defects outside of the heart. For example, multiple bubble studies with progressively larger bubbles may be employed to detect and assess pulmonary shunts, aneurysms, plaque buildup or other narrowing of vessels, spasm or constriction of vessel, or other conditions. In addition, many modifications may be made to adapt a particular situation or material to the teachings provided herein without departing from the essential scope thereof. Therefore, it is intended that the scope not be limited to the particular aspects disclosed but include all aspects falling within the scope of the appended claims.

What is claimed is:

1. A method comprising:
   intravenously directing first bubbles into a patient's venous circulatory system and to a right side of the patient's heart, the first bubbles having sizes that fall within a first range;
   monitoring the patient's heart, with ultrasound imaging, and detecting presence of the first bubbles on a left side of the patient's heart;
   after detecting of the first bubbles on the left side of the patient's heart, intravenously directing second bubbles into the patient's venous circulatory system and to the right side of the patient's heart, the second bubbles having sizes that fall within a second range, the second range having sizes that are greater than sizes in the first range;
   monitoring the patient's heart, with ultrasound imaging, and detecting presence of the second bubbles on the left side of the patient's heart;
   after detecting of the second bubbles on the left side of the patient's heart, intravenously directing third bubbles into the patient's venous circulatory system and to the right side of the patient's heart, the third bubbles having sizes that fall within a third range, the third range having sizes that are greater than sizes in the second range;
   monitoring the patient's heart, with ultrasound imaging, and detecting presence of the third bubbles on the left side of the patient's heart; and
   after detecting of the third bubbles on the left side of the patient's heart, surgically closing a shunt in the patient's heart using a catheter-delivered percutaneous closure device.

2. The method of claim 1, wherein intravenously directing the first bubbles comprises injecting an agitated solution of saline or dextrose into a median cubital vein of the patient.

3. The method of claim 1, wherein monitoring the patient's heart with ultrasound imaging comprises conducting either a transthoracic echocardiogram (TTE) or a transesophageal echocardiogram (TEE).

4. The method of claim 1, wherein the first range comprises bubbles having diameters approximately between 8 um and 15 um.

5. The method of claim 4, wherein the second range comprises bubbles having diameters approximately between 15 um and 25 um.

6. The method of claim 5, wherein the third range comprises bubbles having diameters approximately between 25 um and 35 um.

7. A method comprising:
   intravenously directing first bubbles into a patient's venous circulatory system and to a right side of the patient's heart, the first bubbles having sizes that fall within a first range;
   monitoring the patient's heart, with ultrasound imaging, and detecting presence of the first bubbles on a left side of the patient's heart;
   after detecting of the first bubbles on the left side of the patient's heart, intravenously directing second bubbles into the patient's venous circulatory system and to the right side of the patient's heart, the second bubbles having sizes that are greater than sizes in the first range;
   monitoring the patient's heart, with ultrasound imaging, to detect presence of the second bubbles on the left side of the patient's heart;
   if the presence of the second bubbles is not detected on the left side of the patient's heart, then administering a prophylactic medication; and
   if the presence of the presence of the second bubbles is detected on the left side of the patient's heart, then surgically closing a shunt in the patient's heart.

* * * * *